United States Patent [19]
Taylor et al.

[11] Patent Number: 5,378,345
[45] Date of Patent: * Jan. 3, 1995

[54] CERAMIC SOLID ELECTROLYTE-BASED ELECTROCHEMICAL OXYGEN CONCENTRATOR CELL

[75] Inventors: Dale M. Taylor; Ashok V. Joshi, both of Salt Lake City, Utah

[73] Assignee: Ceramatec, Inc., Salt Lake City, Utah

[*] Notice: The portion of the term of this patent subsequent to Jun. 4, 2008 has been disclaimed.

[21] Appl. No.: 710,128

[22] Filed: Jun. 4, 1991

Related U.S. Application Data

[63] Continuation-in-part of Ser. No. 432,919, Nov. 6, 1989, Pat. No. 5,021,137, which is a continuation-in-part of Ser. No. 156,549, Feb. 16, 1988, Pat. No. 4,879,016, which is a continuation-in-part of Ser. No. 889,214, Jul. 25, 1986, Pat. No. 4,725,346.

[51] Int. Cl.⁶ ............................................. G01N 27/417
[52] U.S. Cl. .................................. 204/421; 204/130; 204/153.18; 204/242; 204/424; 264/58; 264/61
[58] Field of Search ................. 204/143.18, 421–429, 204/242, 263, 265, 266, 130

[56] References Cited

U.S. PATENT DOCUMENTS

| | | | |
|---|---|---|---|
| 3,481,855 | 12/1969 | Kolodney et al. | 204/422 |
| 3,922,204 | 11/1975 | Tseung et al. | 204/153.18 |
| 4,257,863 | 3/1981 | Hoffman | 204/429 |
| 4,283,441 | 8/1981 | Haecker et al. | 204/424 |
| 4,359,374 | 11/1982 | Sano et al. | 204/429 |
| 4,412,904 | 11/1983 | Rohr et al. | 204/424 |
| 4,547,281 | 10/1985 | Wang et al. | 204/426 |
| 4,610,867 | 9/1986 | Seiyama et al. | 204/424 |
| 4,720,335 | 1/1988 | Fukishima et al. | 204/424 |
| 4,725,346 | 2/1988 | Joshi | 204/130 |
| 4,879,016 | 11/1989 | Joshi | 204/424 |
| 5,021,137 | 6/1991 | Joshi et al. | 204/242 |

*Primary Examiner*—T. Tung
*Attorney, Agent, or Firm*—Trask, Britt & Rossa

[57] ABSTRACT

The invention is a ceramic solid electrolyte based electrochemical oxygen concentrator cell and the method for fabricating said cell. The cell is based on a doped cerium oxide ceramic solid electrolyte and lanthanum strontium cobaltite ceramic electrodes.

8 Claims, 6 Drawing Sheets

CERAMIC SOLID ELECTROLYTE-BASED ELECTROCHEMICAL OXYGEN CONCENTRATOR CELL

RELATED APPLICATIONS

This application is a continuation-in-part of U.S. patent application Ser. No. 432,919 filed on Nov. 6, 1989, now U.S. Pat. No. 5,021,137, which was a continuation-in-part of U.S. patent application Ser. No. 156,549, filed on Feb. 16, 1988, now U.S. Pat. No. 4,879,016, which was a continuation in part of U.S. patent application Ser. No. 889,214, filed Jul. 25, 1986, now U.S. Pat. No. 4,725,346.

BACKGROUND OF THE INVENTION

1. Field

This invention generally relates to oxygen generating devices and particularly to electrochemical oxygen generating devices using metal oxide, oxygen ion conducting electrolyte.

2. State of the Art

Electrochemical devices which employ oxygen ion conducting electrolytes are well known. Such devices are used as sensors whereby the oxygen partial pressure difference existing between opposite sides of said electrolyte create a voltage potential which may be determined to indicate a level of oxygen concentration on one side or the other, especially when the oxygen concentration on one side of the sensor is known. Such sensors are used in automobile engines, furnaces and other devices wherein it is desired to operate at stoichiometric ratios between the fuel and the air or oxygen necessary for combustion of fuel.

Also, such electrochemical devices, when operated in a current mode with an applied voltage may be utilized to generate pure oxygen. Devices of this type are discussed in certain patents to Ruka, for example, Re. 28,792.

Certain difficulties have generally been encountered with such oxygen sensors and oxygen generating devices. In electrochemical sensors it is common practice to utilize platinum as an electrode or to utilize various electrode layers, for example, a platinum electrode adjacent to the electrolyte with an overcoating of a protective porous film. Platinum has been generally employed because of its catalytic activity and because of its relatively high melting point among conductive metals. It has been found, however, that the use of platinum in oxygen generating electrochemical cells that the platinum, which is relatively conductive, has an apparent resistance higher than what would normally be expected. Thus, oxygen generating electrochemical cells utilizing platinum electrodes have been electrically inefficient. Furthermore, the platinum electrodes must be porous in order to permit oxygen molecules to reach the surface of the electrolyte at the cathodes, and, upon recombination at the anode surface, to depart from the electrolyte. While pores are thus necessary, the effective electrode-electrolyte interface for electrical purposes is consequently reduced.

Sensors generally are quite small, frequently formed as a disk smaller than a dime or as a thin thimble having a length of about one-half inch and an outside diameter of less than one-fourth inch. The amount of volt-age or current applied or produced by sensors is very small, generally being in the millivolt and milliamp range. The problems of uniform current distribution over a broad area is generally not encountered because of the small size of the device.

The aforementioned patents of Joshi describe many of the considerations involved in producing useful oxygen delivery devices and further describe certain advantageous electrode/electrolyte systems.

Sensors are produced to maximize response time, to endure repeated hot/cold cycling, to be reliable over an extended period of time. Maximizing the quantity of oxygen transported through the electrolyte per amp applied is generally not a factor in sensor design or fabrication.

An oxygen delivery device, while employing oxygen conducting electrolytes and current carrying electrodes, has different objectives than a sensor and involves different considerations. An oxygen delivery device employing larger electrolytes has a very large surface area in comparison to a sensor. Because of the size of the electrolyte, strength is an important factor. Also, the problems of differential temperatures may create stress problems, especially if an area of an electrolyte begins conducting more oxygen ions than other areas, which results in hot spots. A hot spot may be a result of uneven distribution of current by the electrode or a thin wall spot on the electrolyte.

While platinum has generally been the standard electrode for zirconia-type sensors, its use in oxygen delivery devices has been generally unsatisfactory.

SUMMARY OF THE INVENTION

The instant invention relates to an oxygen delivery device having exceptional oxygen-producing capacity per unit area of electrolyte. A unique aspect of the invention involves an electrolyte assembly comprising a doped cerium oxide (ceria) electrolyte in combination with a pervoskite material electrode, especially lanthanum strontium cobaltite (LSCo), adherent to the electrolyte. Preferably, the pervoskite electrode has an overlayer of silver to enhance operation at low temperatures, i.e., less than about 800° C., and an intermediate layer of a mixture of LSCo and an alloy of silver and palladium.

The oxygen delivery devices of this invention are solid state electrochemical cell having air or a mixed gas containing free oxygen on the cathode side of the electrolyte so that under the influence of a direct current, oxygen ions are transported through the electrolyte to be released (pumped) at the anode as oxygen gas. The device may be used to produce pure oxygen or to remove oxygen, as a contaminant, from a gas.

This invention has performance characteristics that far exceed the existing oxygen concentrator cell system based on doped zirconium oxide ceramic electrolyte and lanthanum strontium manganite ceramic electrodes. The performance of electrochemical oxygen delivery cells of certain electrolyte thickness is characterized by the current density of the cell at set voltages and temperatures during operation and the faradaic efficiency, a measure of cell oxygen pumping efficiency. An existing cell employing a 1.0 mm thick zirconia electrolyte operates at a current density of 115 mA/cm$^2$ at a faradaic efficiency of 100% at 800° C. and 1.0 volts do bias potential. Cells with 1.0 mm thick electrolyte fabricated with the materials and method of this invention exhibit a current density of 160 mA/cm$^2$ and 100% faradaic efficiency at 750° C. and 0.5 volts do bias which is equivalent to 430 mA/cm$^2$ and 100% faradaic efficiency at 800° C. and 1.0 volts do bias, a current density 274% greater than obtained with the previous cell.

Electrochemical oxygen delivery cells produced with this invention exhibit oxygen pumping performances far greater than obtained with existing systems.

DETAILED DESCRIPTION OF THE ILLUSTRATED EMBODIMENT

Ceramic solid electrolyte based electrochemical oxygen concentrator cells (SEOC), also referred to as delivery devices, are used for the production of oxygen concentrators producing high purity oxygen. The concentrators separate oxygen from ambient air or $O_2$ enriched air to supply a flow of about 99% to 100% pure oxygen. These concentrators are useful in the medical, aerospace, defense, semiconductor, and utilities industry. The advantage of solid electrolyte base electrochemical oxygen concentrators over the existing pressure swing adsorption systems (PSA) are 1) production of higher purity oxygen (>99% for electrochemical based systems as opposed to <95% for PSA based systems), 2) lower maintenance requirements (once per year for electrochemical systems as opposed to 4 times per year for PSA systems), 3) simplicity of operation, 4) weight, 5) size, and 6) lower operating costs.

The basis of operation of SEOC's is the oxygen ion conductivity of the ceramic solid electrolyte. The ceramic solid electrolyte traditionally used for the production of SEOC cells is cubic phase zirconium oxide doped with yttrium oxide and ytterbium oxide. This material is a pure oxygen ion conductor implying that the charge carrier used in electrical current flow are oxygen ions as opposed to electrons, the charge carrier for electronically conductive materials. The oxygen ion conductivity of doped zirconium oxide is highly temperature dependent, thus the material must be heated to temperature greater than 700° C. before appreciable oxygen ion conductivity is achieved. The normal operating temperature of SEOC cells using zirconium dioxide electrolyte is 800° C. or more.

The electrolyte/electrode assemblies of the instant invention have improved oxygen ion transport over a wide range of temperatures in comparison with traditional electrolyte/electrode assemblies.

Figure 1:
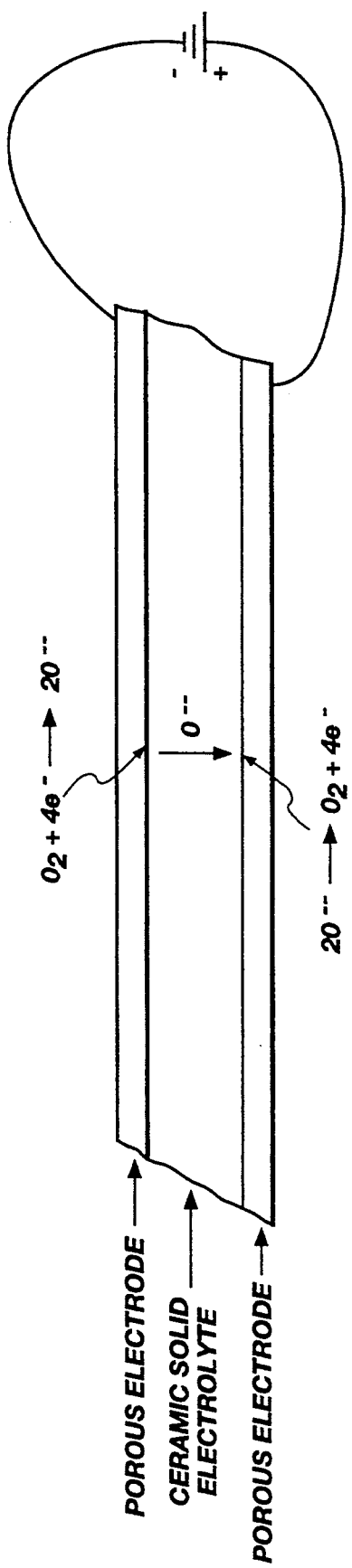
FIG. 1 is a schematic view of an electrolyte assembly of an electrochemical oxygen generating device.

For the SEOC cell to function, an electronically conductive material (cathode) must be applied to the electrolyte material to provide an interface where gaseous oxygen molecules can pick up electrons and be "ionized" to provide oxygen ions for conduction. An interface of this nature must also be present on the other side (anode) of the electrolyte to facilitate the removal of electrons from the oxygen ions to produce oxygen molecules. A schematic illustrating this concept is shown in FIG. 1. In the instant invention, an especially suitable electrode material for this purpose is a porous lanthanum strontium cobaltite ceramic adherent to the electrolyte in conjunction with an intermediate layer and a silver top layer, with all layers preferably being porous. This material has a relatively high electronic conductivity as well as high catalytic activity for oxygen. This ceramic material is also chemically and mechanically compatible with doped cerium oxide ceramic solid electrolytes. The pores within such an electrode material permit gaseous oxygen to be present at the electrode/electrolyte interface.

Figure 2:
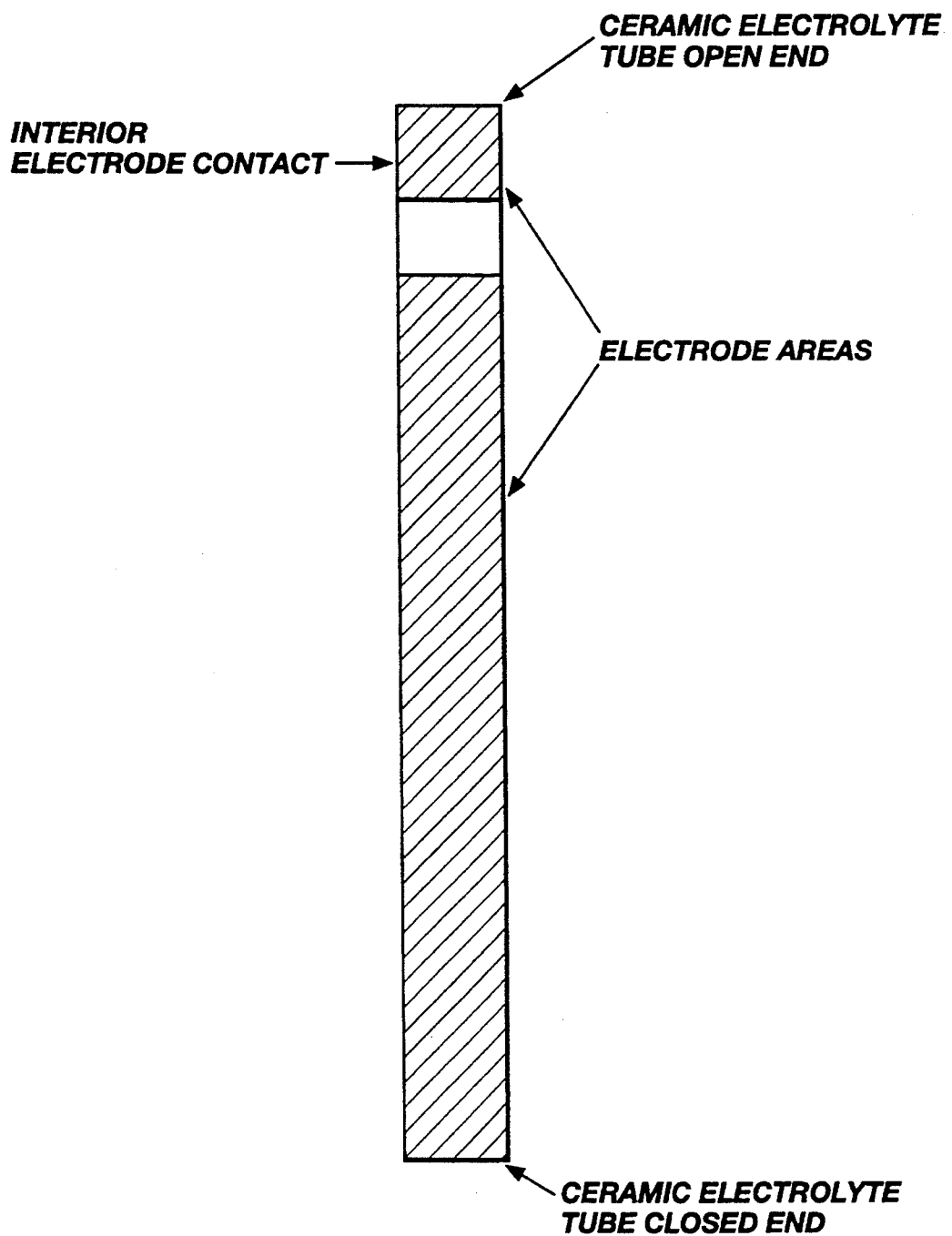
FIG. 2 is an elevational view of a tubular ceramic electrolyte.

As shown in FIG. 1, a do voltage bias is applied across the ceramic electrolyte via the electrode material at high temperatures. In the presence of an oxygen containing gas such as air, oxygen ions are conducted through the electrolyte material and recombine to form pure oxygen on the other side. As shown in FIG. 2, the ceramic solid electrolyte cell is in a tubular form with one closed end to facilitate manifolding.

Two critical parameters are measured when evaluating the performance of a SEOC cell. These parameters are 1) the current density and 2) the faradaic efficiency. The current density (measured in $mA/cm^2$) is a measure of the amount of current that passes through a unit active area of the cell. The current density is a function of the ionic conductivity of the electrolyte, the electrical conductivity of the electrode, and the catalytic activity of the electrode/electrolyte interface. The current density of a cell increases with increases in all the above parameters. The current density is measured by measuring the amount of current that passes through a known active area of the cell at a specific temperature and applied do voltage. In the case of evaluating SEOC cells, the chosen temperature is 750° to 800° C. and the chosen do voltage is 0.5 volts to 1.0 volts. Such parameters are important in defining the amount of active cell area and electrical power required to produce a desired flow rate of pure oxygen. The higher the current density the more desirable the system for SEOC applications. A traditional system based on zirconium dioxide based electrolytes yielded a current density of 115 $Ma/cm^2$ at 800° C. and 1.0 volts bias. The minimum requirement for commercial application of SEOC cells is a current density of 100 $mA/cm^2$ at 800° C. and 1.0 volts. Higher values are more desirable.

The second critical parameter is the faradaic efficiency (expressed in $cm^3$ of $O_2$/min/amp). The faradaic efficiency is a measure of the amount of oxygen flow produced by each amp of current passing through a SEOC cell. For the case of an SEOC cell operating at sea level ambient pressure (1.0 atm) and delivering room temperature (25° C.) oxygen to the flow measurement system, the faradaic efficiency is 3.77 $cm^3$ of $O_2$/min/amp when all of the current flowing through the SEOC cell is due to the conduction of oxygen ions. In this case, the faradaic efficiency is said to be 100%. A faradaic efficiency of 100% is required for SEOC cells as this would indicate that all of the current passed goes to separating oxygen from air and thus has a 100% electrical efficiency. This is the case for SEOC cells based on the existing zirconium dioxide ceramic electrolyte system.

The instant invention is an improvement upon existing electrode-electrolyte assemblies useful in oxygen delivery systems. The invention involves a ceria-based electrolyte doped with calcia and preferably having a rare earth oxide dopant, for example, yttria, ytterbia and the like. Minor quantities of other ingredients may be incorporated to enhance the structural properties of the electrolyte. For example, minor quantities of $ZrO_2$, $HfO_2$ and the like may be utilized as well as minor amounts of alumina, mullite and like ceramic oxides to enhance sintering or structural properties.

The ionic conductivity (mobility of the oxygen ion) of the ceria electrolytes of this invention is significantly better than zirconia or hafnia electrolytes, for example, or even certain ceria or bismuth oxide electrolytes. The enhanced ionic conductance of these improved ceria/calcia/rare earth oxide electrolytes is matched with improved electrodes to achieve a significantly improved electrode/electrolyte assembly which achieves significantly improved current densities, e.g. from about 100 $mA/cm^2$ at 800° C. and 1.0 volts to about 160 $mA/cm^2$ at 750° C. and 0.5 volts and improved faradaic efficiencies, e.g. at about 100%.

The improved electrode system is, preferably, a three-layer electrode wherein the first layer is a porous coating of lanthanum strontium cobaltites (LSCo) adherent to the ceria-based electrolyte. A second or intermediate layer adherent to the first layer is a porous coating of a composite mixture of LSCo and an alloy of Ag (silver) and Pd (palladium) preferably 70% to 80% Pd. A third or surface layer of silver is adherent to the second layer. The top layer is preferably porous. While silver is permeable to oxygen molecules, the high volume oxygen throughput of the electrode/electrolyte assemblies of this invention is generally so great that a porous silver overcoat layer is preferred. A thin, non-porous silver overcoat combined with an adherent silver mesh may be effectively utilized as a good distributor of electrical current to the entire electrode surface, although a porous silver layer is preferred.

The porosity in the electrode is achieved by firing the first and second electrode ink layers at a temperature high enough to cause the LSC and/or Ag/Pd particles to fuse together to form a near continuous or fully continuous sheet without completely sintering to form an impermeable layer. The first and second layers can be cofired or fired individually provided the firing of the second layer is sufficient to cause it to fuse partially, or bond, to the first layer while still remaining porous. The ink for forming the first layer of the electrode is made up of small particles of LSCo suspended in an organic binder. The ink for forming the second layer of the electrode is made up of a mixture of small LSCo particles Ag/Pd alloy particles, or Ag particles and Pd particles, suspended in an organic binder.

The preferred firing temperature of both layers is the same or close to one another to assure that the LSCo particles in the second layer will partially fuse (bond) to the LSCo particles comprising the first layer. The preferred firing temperatures of the first and second layers is between 1110° and 1140° C.

After the first and second layers have been fired on, the third layer (Ag layer) is applied as an ink and fired onto the second layer at a temperature high enough to cause the Ag particles with the Ag ink to partially fuse (bond) to one another and the LSCo and Ag/Pd particles of the second layer, but also fired at a low enough temperature to prevent the Ag particles from fully melting to form a sintered sheet of silver. The firing temperature cannot exceed 955° C. The preferred firing temperature is 800° C.

The preferred thickness of each layer is as follows:
First porous layer—from about 3 $\mu m$ to about 12 $\mu m$
Second porous layer—from about 3 $\mu m$ to about 12 $\mu m$
Third porous layer—from about 5 $\mu m$ to about 100 $\mu m$ The porosity of each layer is generally about the same and ranges from about 40% to about 80%. (Porosity is generally indicated as vol. % of pores, i.e., voids). The pores are generally channels through the electrode material to permit the rapid passage of oxygen molecules therethrough to contact the electrolyte surface.

The desired porosity of the electrode materials may be obtained by the inclusion of a desired amount of combustible particles which readily burn off at or below the firing temperature of the electrode and/or electrolyte to leave a void. Preferably, such combustible particles do not leave any residue. Suitable combustible particles include carbon and/or organic particles. Also, a combustible organic binder or organic carrier used to make a slurry of the electrode material to facilitate application to the electrolyte effectively creates pores when burned out during a firing process. Firing of the electrodes are generally conducted at a temperature and for a time period which does not fully sinter the material to a density at or near 100%. For the electrode materials of the instant invention, firing time of about 30 minutes to about 3 hours at temperatures of $\sim 1125° \pm 15°$ C. yield electrode with an appropriate range of porosity.

The composition of the first layer is preferably pure lanthanum strontium cobaltite, although very minor quantities of other materials, especially oxides, may be included. Examples of such additional materials include copper oxide in quantities up to about 10% by weight.

The composition of the intermediate layer is generally about 25-75 mole % of LSCo and about 75-25 mol % Ag/Pd alloy. A preferred mixture is about 25% LSCo and 75% alloy. The Ag/Pd alloy is preferably about 70 wt. % Ag and about 30 wt. % Pd. The alloy is effective at wt. ratios of about 60-80 Ag and 40-20 Pd. Small quantities of other materials such as copper oxide, lanthanum strontium manganite (LSM) and the like may be included. The surface (top) layer is preferably pure silver with about the same porosity as the bottom and intermediate electrode layers. Minor quantities of other materials such as copper or copper oxide, palladium, LSCo, LSM, and the like may be included.

The invention relates to the composition and method of fabrication for producing thin wall (0.022") SEOC cells based on a calcium oxide and yttria oxide doped cerium oxide solid electrolyte and a lanthanum strontium cobaltite ceramic electrode. SEOC cells produced using this invention exhibit a mean current density of 232 $mA/cm^2$ and a faradaic efficiency of 3.77 $cm^3$ of $O_2$/min/amp at 720° C. and 0.500 volts dc operating voltage. This current density exceeds the current density of the thick wall (1.0 mm) zirconia-based SEOC system by several fold. Thus, an electrolyte assembly comprising a doped ceria electrolyte in conjunction with a lanthanum strontium cobaltite electrode is a more desirable system for the production of SEOC units since such a high current density at lower temperatures and cell voltages implies a reduction in size and power consumption of a unit relative to units based on a zirconia-based system.

EXAMPLE I

The first procedure in fabricating SEOC cells sing this invention is to fabricate cell tubes out of CaO/Y$_2$O$_3$-doped cerium oxide electrolyte material. The starting material is a powder prepared in the following manner. Calcium carbonate, yttria, and cerium dioxide powders are weighed to create a composition in the region of 0.05–20.0 m/o CaO, 99.5–75.0 m/o cerium oxide and about 0.009–5.0 m/o yttria, then placed in a ball mill for mixing. A preferred mixture is one providing the composition: $Ca_{0.1}Y_{0.02}Ce_{0.88}O_x$. The ball mill contains zirconium oxide milling media and water containing a dispersant. The amount of water is kept to a level whereby the slurry formed during mixing is 80% solids. The materials are mixed for 2–4 hours before being poured into heated trays for drying.

After drying, the resultant powder cake is pulverized and passed through a 40 mesh sieve. The sieved powder is placed into aluminum oxide crucibles and prereacted at temperatures between 1200° and 1450° C.

After firing, the prereacted powder is ball milled to reduce its particle size in a plastic ball mill containing zirconium oxide milling media and enough water to produce a slurry containing 67% solids. The material is milled for 16 hours before a ceramic binder material is added in a proportion of 1–3 w/o. The milling is continued for one more hour before the slurry is poured into heated trays for drying.

After the material is dried, it is crushed and passed through a 40 mesh sieve. After sieving, the material is placed into an isostatic pressing die to form a closed ended tube 6" long by ½" in diameter. The pressing pressure is between 15,000 and 30,000 psi and maintained for 1–3 minutes.

After pressing, the green tubes are drilled near the closed end. A zirconia or alumina pin is inserted through the drilled hole and the green tube is suspended in the sintered furnace. The tubes are placed in a high temperature furnace and fired at a heating rate between 50 and 100° C./hr. to 1400°–1600° C. and held at temperature for 2–5 hours.

After firing, tubes are cut to length, inspected for defects and density and are ready for the electrode application process.

The lanthanum strontium cobaltite (LSC) ceramic electrode material is prepared using the same mixing and milling procedures as above. Lanthanum carbonate, strontium carbonate, and cobalt oxide are weighed in such proportions to yield a final composition of 0.10–0.40 m/o lanthanum oxide (La$_2$O$_3$), 0.20–0.80 m/o strontium carbonate, and 1.0 m/o cobalt oxide. The prereaction temperature used is between 900° and 1200° C. for 2–6 hours. The particle size reduction milling procedure is for 24 hours and uses ethanol instead of water. No binders are added during this procedure.

After milling and drying, an ink paste is prepared using the resultant powder and a composition containing 32–40 w/o polyvinyl butylral (PVB) binder and 60–68 w/o terpineol solvent. The solids content is 50–60 w/o.

The LSC ink is applied to the doped cerium oxide ceramic electrolyte tube using a paint brush on interior and the exterior in the pattern shown in FIG. 2.

After the LSC electrode ink is applied to both the exterior and interior surfaces of the tube, the ink is dried by blowing warm over and through the tube. After drying, the tubes are placed in a furnace and fired to a temperature between 1000° and 1200° C. for 1–4 hours to form the electrode/electrolyte interface and bond the LSCo electrode material to the doped cerium oxide ceramic electrolyte tube.

Once the film of LSCo material has been applied, a layer of LSCo/alloy of silver/palladium is applied to both interior and exterior surfaces in the manner described above, and fired to a temperature between 1000° and 1200° C. for 1–4 hours. An overcoat of silver is applied as a silver paste which is fired at a temperature of 700–850° C. The silver layer is applied to serve as a current collecting electrode to distribute current evenly over the entire area when a voltage is applied during operation.

Once all the electrode layers have been applied and fired, the cell is ready for manifolding and operation.

EXAMPLE II

Figure 3:
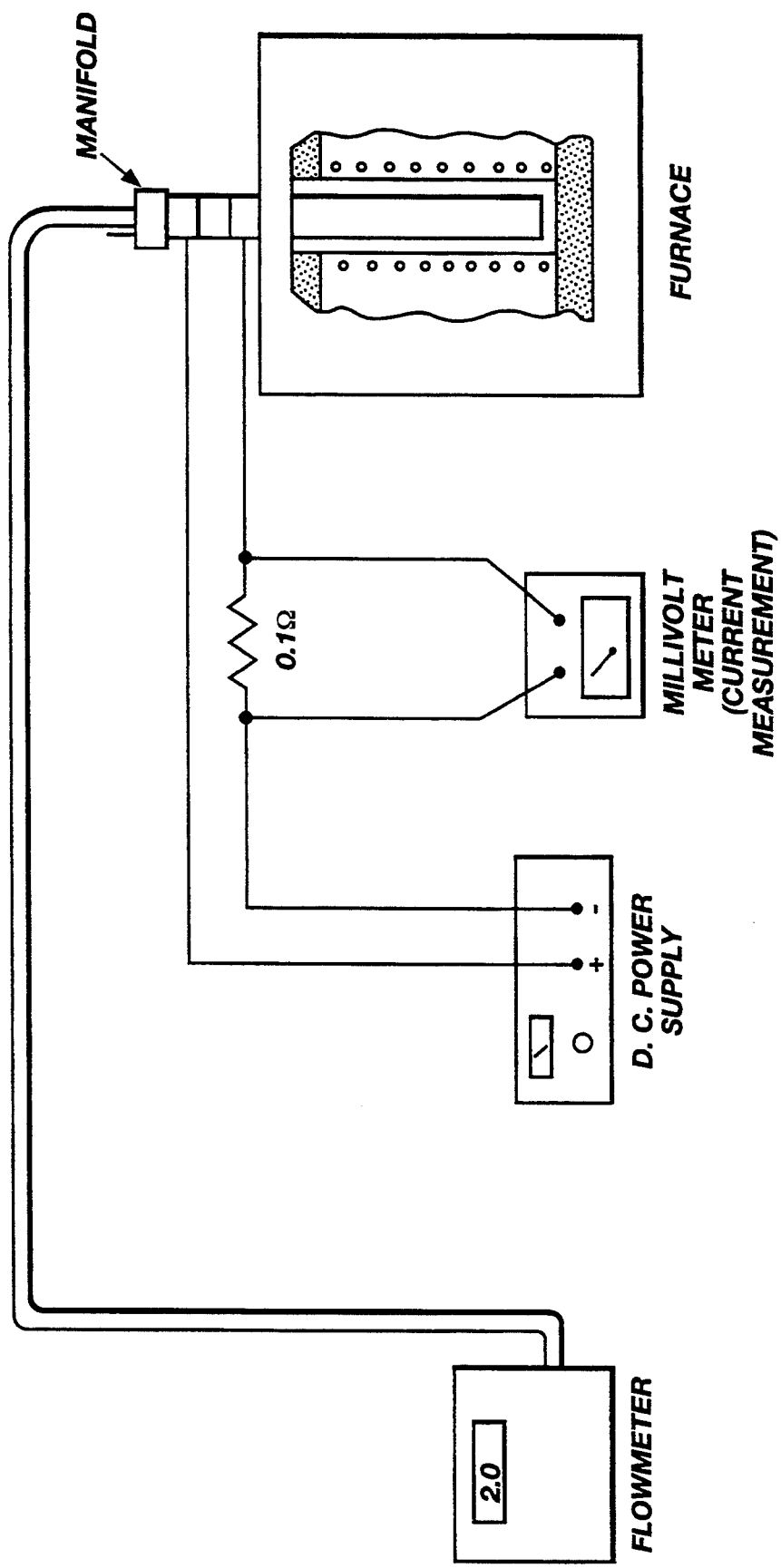
FIG. 3 is a schematic representation of an electrochemical oxygen generating system.

Evaluation:

The completed cells are evaluated using the test setup shown schematically in FIG. 3. The setup consists of a furnace capable of operation to 850° C., a direct current (dc) power supply rated for a 0–5 volt, 15 amp output, a—voltmeter, and an instrument for measuring oxygen flow rate.

The manifold cell to be evaluated is plumbed out of the furnace and connected to tubing to supply oxygen flow to the flow rate measurement system. Electrical contact is made in such a way as to provide a positive bias on the tube interior and a negative bias on the tube exterior. The cell is then placed into the furnace in such a way as to have a known amount of active cell area in the constant temperature zone of the furnace. The cell is heated to temperatures between 500° and 800° C. in 100° C. increments, a measurement of current density vs. voltage and oxygen flow rate being made at each temperature.

The current density is measured as a function of the applied dc voltage. Once the cell is at the temperature of interest, voltage is applied using the dc power supply and current measured by measuring the voltage drop across a 0.1 ohm or 0.005 ohm resistor in series with the cell. Current is measured at 0.20, 0.50, 0.75, and 1.00 volts. Oxygen flow rate is also measured at each voltage to insure faradaic efficiency. The current density is calculated by dividing the cell current by the active cell area. In the case of the cells fabricated using this invention, the active surface area was 22.1 cm$^2$.

Figure 4:
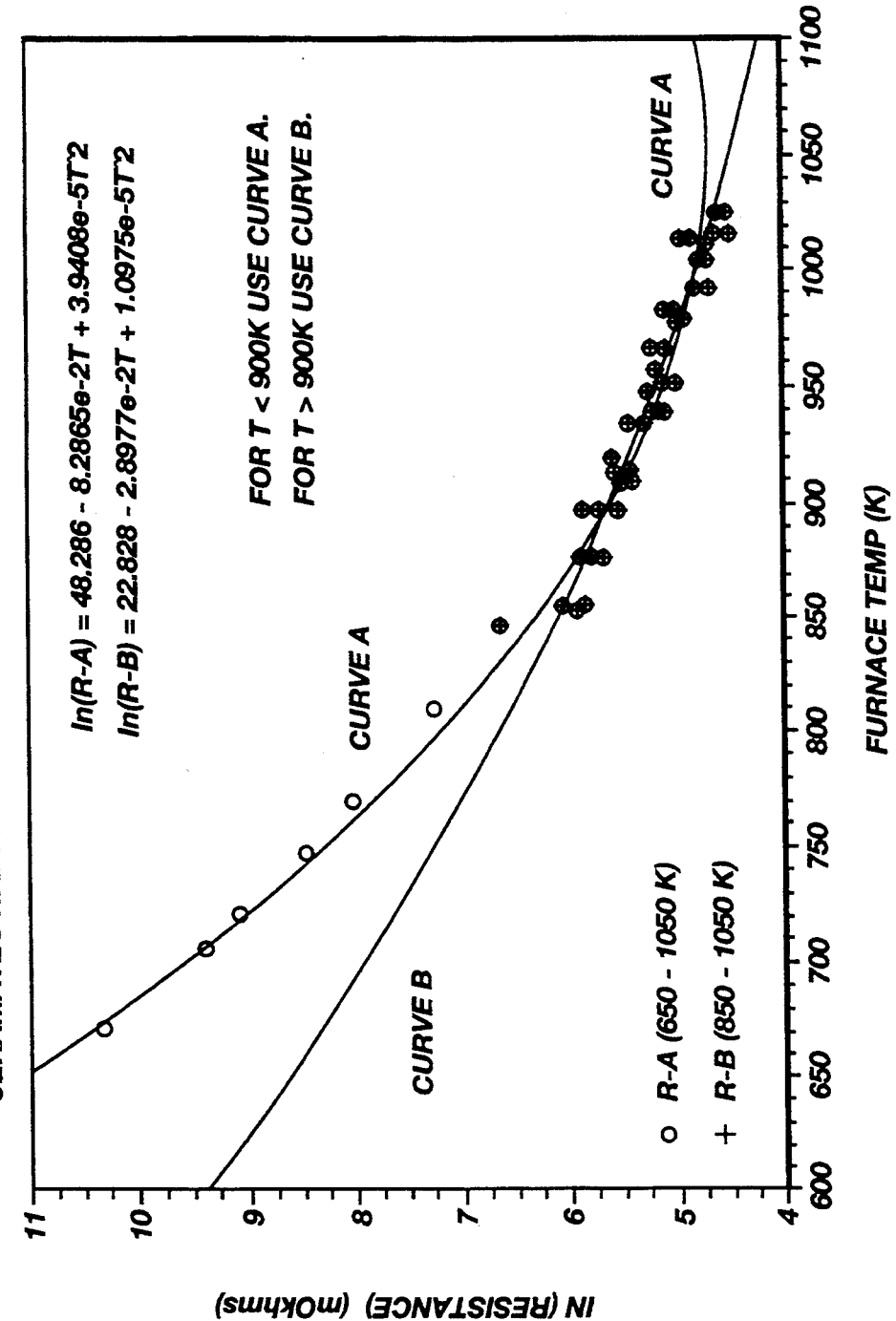
FIG. 4 is a chart illustrating the effect of temperature upon ionic resistivity for a cerium oxide/electrode cell of the instant invention.
Figure 5:
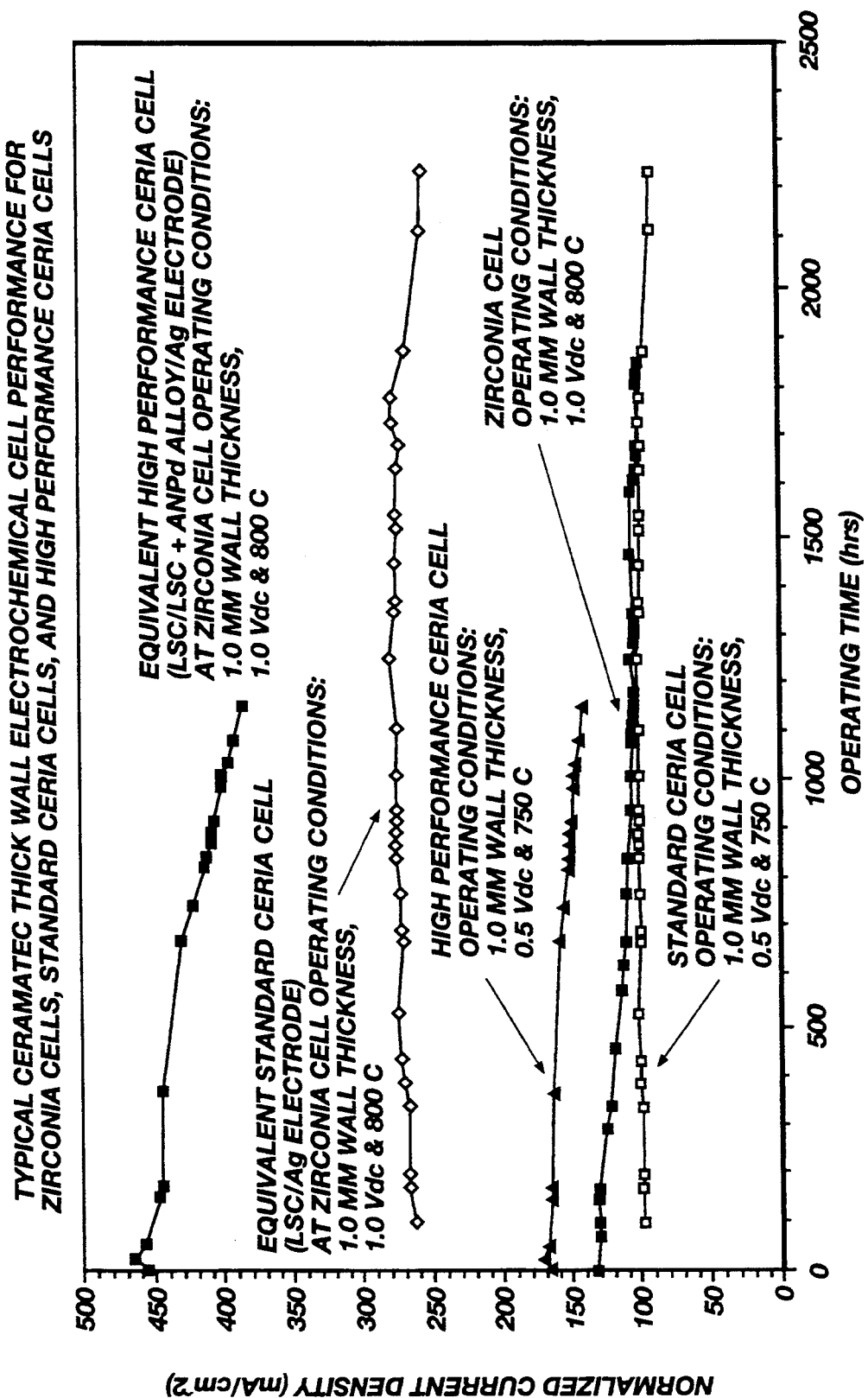
FIG. 5 is a chart illustrating the improved current density for an electrochemical cell of the instant invention as compared with previously existing cells.

FIG. 4 is a chart illustrating the effect of temperature upon cell resistance of a cell (electrode/electrolyte assembly) of the type described in Example I. For comparison purposes, FIG. 5 compares the current density vs. voltage characteristics at 800° C. for a cell fabricated using the existing zirconium dioxide cell technology with a cell fabricated using this invention. As can be seen in FIG. 5, the thick wall (1.0 mm) cell fabricated using this invention has a current density 290% greater than the cell fabricated using existing technology.

Figure 6:
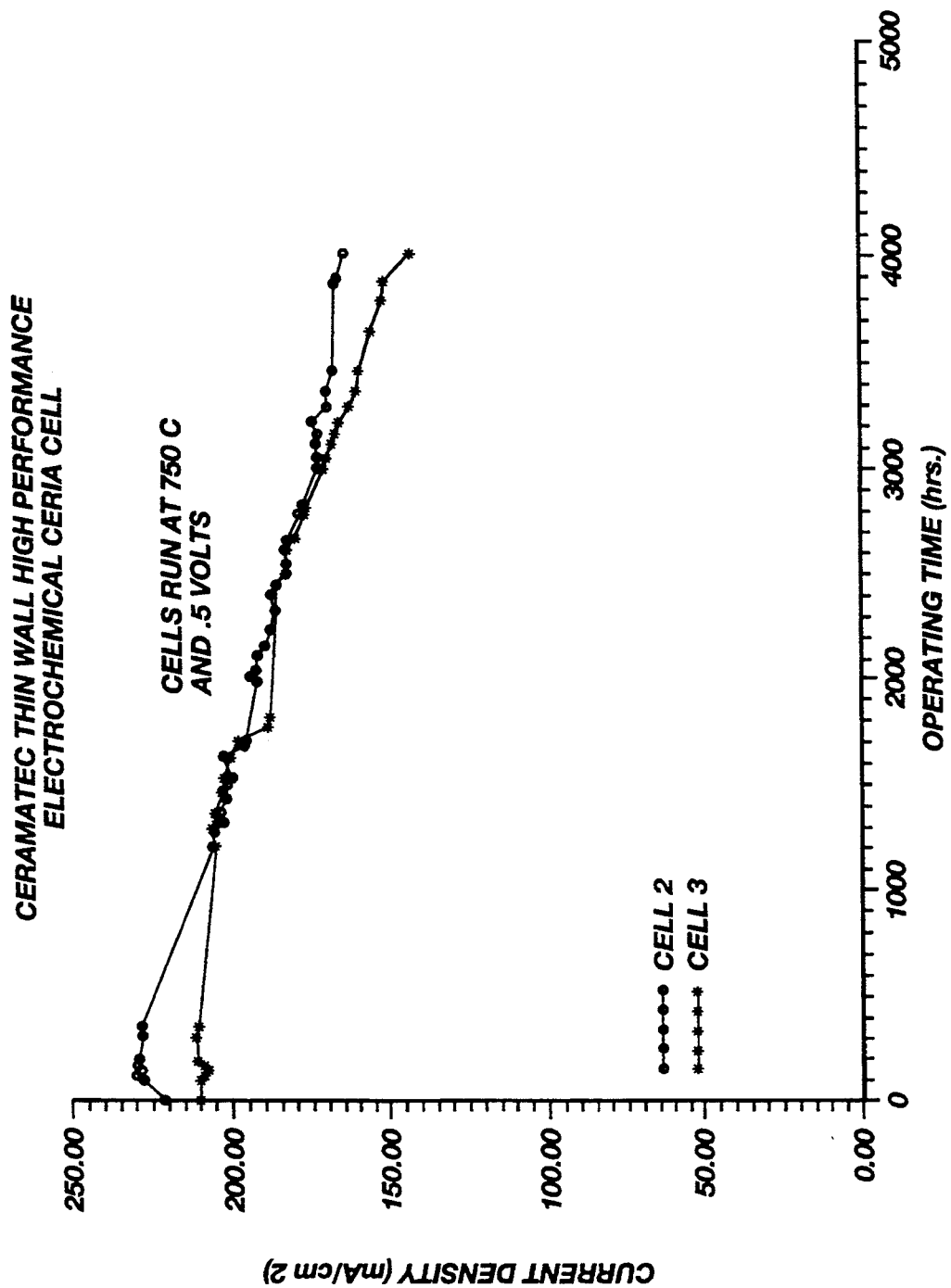
FIG. 6 is a chart showing the stability of current density over an extended period of time for thin-wall, high performance, doped cerium oxide-based electrochemical cells.

FIG. 6 illustrates the stability (uniformity) of current density over an extended period of time for an electrochemical cell of the type set forth in Example I.

The electrolyte assemblies of the instant invention generally involve tubes or plates having a surface area from about 20 cm$^2$ to about 40 cm$^2$. The ceria electrolytes are formed by conventional ceramic forming techniques. The electrodes, i.e., the metal oxide materials with pervoskite crystal structure, are usually about 50 to 150 microns in overall thickness, although a thickness of about 70 to about 120 microns is generally preferred. This includes the thickness of the silver overcoat.

The silver, when applied as a very thin film, i.e., about 10±5 microns, is generally non-porous. Thicker silver films (15 microns or greater) are preferably porous. Silver is the preferred overlayer for low temperature ($\leqq 800°$ C.) operation. A small amount of copper, e.g. from about 0.1% to about 5%, may be usefully incorporated in the Ag/Pd alloy in the intermediate and in the silver overcoat.

Other metal overlays useful in the invention include Inconel, Monel, copper alloys, silver alloys, silver or copper-plated Inconel mesh, and the like. Overlays of materials other than silver or a silver alloy must generally contain considerable porosity.

Since there is a direct relationship between current density and the amount of oxygen produced by a device of the instant invention, a perusal of the data in FIGS. 5 and 6 illustrates the difference between oxygen delivery devices and sensors. A sensor generally operates at a current density of less than 10 mA/cm$^2$ while the oxygen delivery devices of this invention generally operate at a current density of at least 100 mA/cm$^2$ and, as seen from FIGS. 5 and 6, current densities greater than 200 are preferred.

Automobile sensors may only operate for a period of a thousand hours. Replacement of sensors is frequently recommended after 50,000 miles, which is about 1000 hrs. operation. An oxygen delivery device, for example, a medical oxygen source, may require operation 24 hours/day for a year or more. The data from FIG. 6 shows continuous operation of an oxygen delivery device of the instant invention at a very high current density for a period in excess of 4000 hours.

Although the invention has generally been described as an electrolyte/electrode assembly, the unique electrode system described herein may be advantageously used with electrolytes other than ceria, for example, zirconia, hafnia, bismuth oxide and the like.

We claim:

1. An electrode/electrolyte combination for an oxygen delivery system for delivering oxygen ions through said electrolyte to produce essentially pure O$_2$ from an O$_2$-containing gas mixture, the improvement comprising:
    a thin walled electrolyte having a pair of opposed surfaces
        consisting essentially of ceria, calcia and yttria;
    a three-layer electrode system, consisting essentially of
        a first thin, substantially continuous layer of LSCo adherent to each surface of said electrolyte,
        a second thin, substantially continuous layer of a composite mixture of LSCo and an alloy of Pd and Ag adherent to said first layer, and
        a third thin, substantially continuous layer of silver adherent to said second layer.

2. The electrode/electrolyte combination of claim 1, wherein said electrolyte is a ceramic composition having about 99.5–75.0 mol. % of CeO$_2$, 0.009– 5.0 mol. % Y$_2$O$_3$ and 0.05–20 mol. % CaO.

3. The electrode/electrolyte combination of claim 2, wherein said electrolyte is a ceramic composition having about 88 mol. % CeO$_2$, 2 mol. % Y$_2$O$_3$ and 10 mol. % CaO.

4. The electrode/electrolyte combination of claim 1 wherein said electrode layers have a porosity of about 40 to 80%.

5. The electrode/electrolyte combination of claim 1 wherein said first electrode layer is about 3 μm to about 12 μm thick; said second electrode layer is about 3 μm to about 12 μm thick and said third electrode layer is about 5 μm to about 100 μm thick.

6. The electrode/electrolyte combination of claim 5 wherein said electrode layers have a porosity of about 40 to 80%.

7. The electrode/electrolyte combination of claim 1 wherein said second electrode layer is about 25–75 mol. % LSCo and about 75–25 mol. % Ag/Pd alloy.

8. The electrode/electrolyte combination of claim 1 wherein said alloy in said second electrode layer is about 60–80 wt % Ag and 40–20 wt % Pd.

* * * * *